United States Patent
Yonekura et al.

(10) Patent No.: US 8,754,935 B2
(45) Date of Patent: Jun. 17, 2014

(54) MICROSTRUCTURE INSPECTION METHOD, MICROSTRUCTURE INSPECTION APPARATUS, AND MICROSTRUCTURE INSPECTION PROGRAM

(75) Inventors: Isao Yonekura, Kuki (JP); Hidemitsu Hakii, Kuki (JP)

(73) Assignee: Toppan Printing Co., Ltd., Tokyo (JP)

( * ) Notice: Subject to any disclaimer, the term of this patent is extended or adjusted under 35 U.S.C. 154(b) by 446 days.

(21) Appl. No.: 12/736,157

(22) PCT Filed: Mar. 19, 2009

(86) PCT No.: PCT/JP2009/055475
§ 371 (c)(1),
(2), (4) Date: Sep. 16, 2010

(87) PCT Pub. No.: WO2009/116634
PCT Pub. Date: Sep. 24, 2009

(65) Prior Publication Data
US 2011/0001816 A1    Jan. 6, 2011

(30) Foreign Application Priority Data

Mar. 19, 2008 (JP) ................................ 2008-071312
Mar. 19, 2008 (JP) ................................ 2008-071315
Sep. 18, 2008 (JP) ................................ 2008-239205
Jan. 14, 2009 (JP) ................................ 2009-005495

(51) Int. Cl.
G01B 15/00 (2006.01)
G01N 23/00 (2006.01)
G21K 7/00 (2006.01)
G01B 15/04 (2006.01)

(52) U.S. Cl.
CPC ................ G01B 15/04 (2013.01); G01N 23/00 (2013.01); G21K 7/00 (2013.01)
USPC .............. 348/80; 250/310; 250/306; 250/307

(58) Field of Classification Search
None
See application file for complete search history.

(56) References Cited

U.S. PATENT DOCUMENTS 6,472,662 B1    10/2002  Archie
7,230,243 B2 *   6/2007  Tanaka et al. ................ 250/310

(Continued)

FOREIGN PATENT DOCUMENTS

JP    2-91504      3/1990
JP    10-170530    6/1998

(Continued)

OTHER PUBLICATIONS

Su et al, "Sidewall Angle Measurement Using CD SEM", Proc. Of IEEE Conf. on Advanced Semiconductor Manufacturing, 1998, pp. 259-261.*

(Continued)

*Primary Examiner* — Jay Au Patel
*Assistant Examiner* — Reza Aghevli

(57) ABSTRACT

A microstructure inspection method which inspects an angle of a sidewall of a sample microstructure pattern, the method including: taking SEM photographs of the sample microstructure pattern under plural SEM conditions; measuring a width of a white band at an edge portion of the sample microstructure pattern in the SEM photographs; and calculating the angle of the sidewall of the sample microstructure pattern on the basis of an amount of change in the width of the white band due to the change between the plural SEM conditions.

10 Claims, 9 Drawing Sheets

(56) References Cited

U.S. PATENT DOCUMENTS

| | | | |
|---|---|---|---|
| 8,053,726 B2* | 11/2011 | Nakasuji et al. | 250/310 |
| 8,188,429 B2* | 5/2012 | Ozawa | 250/311 |
| 2006/0043292 A1* | 3/2006 | Matsui | 250/310 |
| 2007/0051888 A1* | 3/2007 | Rosenberg et al. | 250/310 |
| 2007/0187595 A1* | 8/2007 | Tanaka et al. | 250/307 |

FOREIGN PATENT DOCUMENTS

| | | |
|---|---|---|
| JP | 2000-146558 | 5/2000 |
| JP | 2003-302214 | 10/2003 |
| JP | 2005-77192 | 3/2005 |
| JP | 2010-503931 | 2/2010 |
| JP | 2010-87075 | 4/2010 |
| WO | 2008/034057 A2 | 3/2008 |

OTHER PUBLICATIONS

Korean Notice of Allowance dated Feb. 15, 2012 issued in corresponding Korean Patent Application No. 10-2010-7020751.
International Search Report mailed May 19, 2009 issued in corresponding International Patent Application No. PCT/JP2009/055475.
Japanese Office Action mailed Apr. 3, 2012 issued in corresponding Japanese Patent Application No. 2010-503931.

* cited by examiner

| CONDITIONS | PATTERN A | PATTERN B |
|---|---|---|
| ANGLE OF SIDEWALL |  |  |
| 5pA |  19.9nm |  25.7nm |
| 10pA |  21.0nm |  29.7nm |
| AMOUNT OF CHANGE | 1.1nm | 4.0nm |

*FIG. 7*

| CONDITIONS | PATTERN A | PATTERN B |
|---|---|---|
| ANGLE OF SIDEWALL | | |
| SEM CONDITION 1 | 18.1nm | 25.7nm |
| SEM CONDITION 2 | 18.7nm | 28.9nm |
| AMOUNT OF CHANGE | 0.6nm | 3.2nm |

MICROSTRUCTURE INSPECTION METHOD, MICROSTRUCTURE INSPECTION APPARATUS, AND MICROSTRUCTURE INSPECTION PROGRAM

CROSS REFERENCE TO RELATED APPLICATIONS

This application claims the benefit under 35 U.S.C. Section 371, of PCT International Application Number PCT/JP2009/055475, filed Mar. 19, 2009, which claimed priority to Japanese Application Nos. 2008-071312, filed Mar. 19, 2008, 2008-071315, filed Mar. 19, 2008, 2008-239205, filed Sep. 18, 2008 and 2008-005495, filed Jan. 14,2009, the disclosures of which are hereby incorporated by reference.

TECHNICAL FIELD

The present invention relates to a microstructure inspection unit, a microstructure inspection program, and a microstructure inspection method. More particularly, the present invention relates to a microstructure inspection unit, a microstructure inspection program, and a microstructure inspection method which inspects an angle of a sidewall of a microstructure pattern.

RELATED ART

In recent years, microstructures of various shapes are in wide use. Examples thereof include semiconductor devices, optical elements, wiring circuits, storage devices (e.g., hard disks and DVDs), chips for medical inspection (e.g., for DNA analysis), display panels, micro passages, micro reactors, MEMS devices, imprint molds and photomasks.

In these microstructures, an angle of a sidewall at an edge portion, as well as a two-dimensional line width of a pattern and a pattern configuration, is considered to be important.

For example, a EUV photomask which is expected to be a next-generation mask is a reflective mask that is different from a conventional transmissive photomask. It is therefore necessary to form a sidewall of a pattern edge as close as possible to vertical and thus to measure an angle thereof.

As a method of measuring the angle of the sidewall of these microstructures, it has been proposed to cut out a sample, observe a cross section of the sample using, for example, a scanning electron microscope (SEM) and evaluate the angle of the sidewall.

As an method of measuring such angle of the sidewall of these microstructures, it has been proposed to measure the angle of the sidewall using an atomic force microscope (AFM) with an ingenious shape of a cantilever tip and an ingenious measuring method (for example, see Japanese Unexamined Patent Application, First Publication No. H10-170530).

As a method to check a two-dimensional line width of a pattern and a pattern configuration, use of a critical dimension SEM (CD-SEM) has been known. In the CD-SEM, the electron beam emitted from an electron gun is converged by a condensing lens, made to pass through an aperture and to collide with the pattern to be measured. Secondary electrons emitted at this time are captured by a detector and are converted into electrical signals. Thus a two-dimensional image is obtained. A dimension of a pattern to be measured or other information can be measured highly accurately from the information of the two-dimensional image.

In the SEM, an object is observed in the following manner: an electron ray is converged to form an electron beam which is made to collide with the object; and secondary electrons, reflected electrons, transmission electrons, X-rays, cathode luminescence (fluorescent light), internal electromotive force and other energy emitted from the object are detected. At this time, these signals emitted from the sample object are detected by a detector, and amplified or modulated to be displayed as an SEM photograph.

DISCLOSURE OF THE INVENTION

Problems to be Solved by the Invention

In recent years, a device and a method for the measurement of an angle of a sidewall of a microstructure have been desired.

However, the related method of cutting out a sample and observing using a cross-sectional SEM or other device is a destructive inspection. Naturally, the sample used in the inspection cannot be provided as a product any more. Another approach of preparing separate sample for the evaluation experiment of the sidewall angle, however, also has a problem that the identity of the actual sample and the sample for the evaluation cannot be guaranteed.

In the AFM, it is possible to measure the actual sample itself in a non-destructive manner. However, there is a problem of an extremely low throughput, because the AFM measures the sample by physically scanning it with a needle. Further, as the number of measurement increases, the needle would gradually get worn out and measurement values become inaccurate. Accordingly, there is a problem that the AFM is not suitable for the measurement of the angle of the sidewall of a large number of patterns.

In addition, if the angle of the sidewall of the pattern to be measured is reversely tapered, it is difficult to move the needle of the AFM along the reversely tapered inclination. It is therefore difficult to measure the angle of the sidewall.

An aspect of the present invention has been made to solve the problems described above and an object thereof is to provide a microstructure inspection unit, a microstructure inspection program and a microstructure inspection method that can measure an angle of a sidewall of a microstructure in a suitable manner.

Means for Solving the Problems (1) An aspect of the present invention provides the following method: a microstructure inspection method which inspects an angle of a sidewall of a sample microstructure pattern, the method including: producing SEM photographs of the sample microstructure pattern under plural SEM conditions; measuring a width of a white band at an edge portion of the sample microstructure pattern in the SEM photographs; and calculating the angle of the sidewall of the sample microstructure pattern on the basis of an amount of change in the width of the white band due to the change between the plural SEM conditions.

(2) The above-described microstructure inspection method may be implemented as follows: the plural SEM conditions have mutually different current values of the electron beams.

(3) The above-described microstructure inspection method may be implemented as follows: the plural SEM conditions have mutually different amplification values of the photomultiplier tubes.

(4) The above-described microstructure inspection method may be implemented as follows: the method further includes taking SEM photographs of plural standard microstructure patterns of which angles of the sidewalls are known and then calculating a reference amount of change which is an amount of change in the width of the white band per unit angle of the sidewall.

(5) The above-described microstructure inspection method may be implemented as follows: the method further includes calculating a reference amount of change, which is an amount of change in the width of the white band per unit angle of the sidewall, using a SEM simulator.

(6) The above-described microstructure inspection method may be implemented as follows: the method further includes causing the electron beam and the sample to be tilted relative to each other if the amount of change in the width of the white band of the sample microstructure pattern is smaller than a predetermined value, and repeating taking of the SEM photographs; and correcting the tilt angle with respect to the angle of the sidewall of the calculated sample microstructure pattern.

(7) The above-described microstructure inspection method may be implemented as follows: the calculating the reference amount of change includes: under two SEM conditions, taking the SEM photographs of a standard microstructure pattern A of which an angle of the sidewall is known; measuring the width of the white band at the edge portion in the SEM photographs of the standard microstructure pattern A and calculating a difference $\Delta W_A$ in the widths of the white band of the standard microstructure pattern A under the two SEM conditions; under two SEM conditions, taking the SEM photographs of a standard microstructure pattern B, which is different from the microstructure pattern A, of which an angle of the sidewall is known; measuring the width of the white band at the edge portion in the SEM photographs of the standard microstructure pattern B and calculating a difference $\Delta W_B$ in the widths of the white band of the standard microstructure pattern B under the two SEM conditions; and calculating the reference amount of change with the following formula: (Reference amount of change)=$|\Delta W_A - \Delta W_B|/|$(Angle of sidewall of microstructure pattern A)−(Angle of sidewall of microstructure pattern B)$|$.

(8) The above-described microstructure inspection method may be implemented as follows: the calculating the angle of the sidewall of the sample microstructure pattern includes: under the two SEM conditions, taking SEM photographs of the sample microstructure pattern of which angle of the sidewall is not known; measuring the width of the white band at the edge portion in the SEM photographs of the sample microstructure pattern and calculating a difference $\Delta W$ in the widths of the white band under the two SEM conditions; and calculating the angle of the sidewall of the microstructure pattern with the following formula using the reference amount of change, the angle of the sidewall of the pattern B, $\Delta W_B$ and $\Delta W$: (Angle of sidewall of microstructure pattern)=(Angle of sidewall of pattern B)+($\Delta W_B - \Delta W$)/(Reference amount of change).

(9) The above-described microstructure inspection method may be implemented as follows: in the taking the SEM photographs of the microstructure pattern, measurement areas each having a predetermined width are defined along a longitudinal direction of the white band, and distribution of the width of the white band in the measurement areas is measured.

(10) An aspect of the present invention provides the following structure: a microstructure inspection unit which inspects of an angle of a sidewall of a microstructure pattern, the unit including: a sample holding mechanism which fixes a sample provided with a pattern to be measured; a CD-SEM mechanism which takes SEM photographs of the pattern to be measured under plural SEM conditions; an image processing mechanism which obtains a width of a white band at an edge portion of the pattern to be measured from the SEM photographs; and a calculation mechanism which calculates the angle of the sidewall of the pattern to be measured, wherein the calculation mechanism calculates the angle of the sidewall of the pattern to be measured using the amount of change in the width of the white band due to the change between the plural SEM conditions.

(11) The above-described microstructure inspection unit may be implemented as follows: the plural SEM conditions have mutually different current values of the electron beams.

(12) The above-described microstructure inspection unit may be implemented as follows: the plural SEM conditions have mutually different amplification values of the photomultiplier tubes.

(13) The above-described microstructure inspection unit may be implemented as follows: the sample holding mechanism holds the sample in a manner such that a relative angle of incidence of the electron beam with respect to the pattern to be measured during the taking of the SEM photograph is changeable.

(14) The above-described microstructure inspection unit may be implemented as follows: the calculation mechanism further includes an SEM simulator for the calculation of a reference amount of change, which is an amount of change in the width of the white band per unit angle of the sidewall due to the change between the plural SEM conditions.

(15) An aspect of the present invention provides the following program: a microstructure inspection program which inspects an angle of a sidewall of a microstructure pattern, the program including: a routine which obtains SEM photographs of the microstructure pattern taken under plural SEM conditions; a routine which measures a width of a white band at an edge portion of the microstructure pattern in the SEM photographs; and a routine which calculates the angle of the sidewall of the microstructure pattern using an amount of change in the width of the white band due to the change between the plural SEM conditions.

Effect of the Invention

The microstructure inspection unit and the microstructure inspection method according to an aspect of the present invention are characterized by taking SEM photographs under plural SEM conditions and calculating an angle of a sidewall of a microstructure pattern from a width of a white band in the SEM photographs.

After their intensive study, the present inventors found that the angle of the sidewall of the microstructure pattern has a correlation with the current value of the electron beam during taking of the SEM photograph and with the width of the white band in the SEM photograph. With this knowledge, it is possible to calculate the angle of the sidewall of the microstructure pattern by obtaining the current value of the electron beam during taking of the SEM photograph and the value of the width of the white band in the SEM photograph.

In addition, after their intensive study, the present inventors found that the angle of the sidewall of the microstructure pattern has a correlation with an amplification value of a photo-multiplier tube in a secondary electron detector during taking of the SEM photograph and with the width of the white band in the SEM photograph. With this knowledge, it is possible to calculate the angle of the sidewall of the microstructure pattern by obtaining the amplification value during taking of the SEM photograph and the value of the width of the white band in the SEM photograph.

BRIEF DESCRIPTION OF THE DRAWINGS

FIG. 7 illustrates SEM images representing an Example of a microstructure inspection method and measurement results of widths of white bands of the SEM images according to a third embodiment.

REFERENCE NUMERALS

Figure 1:
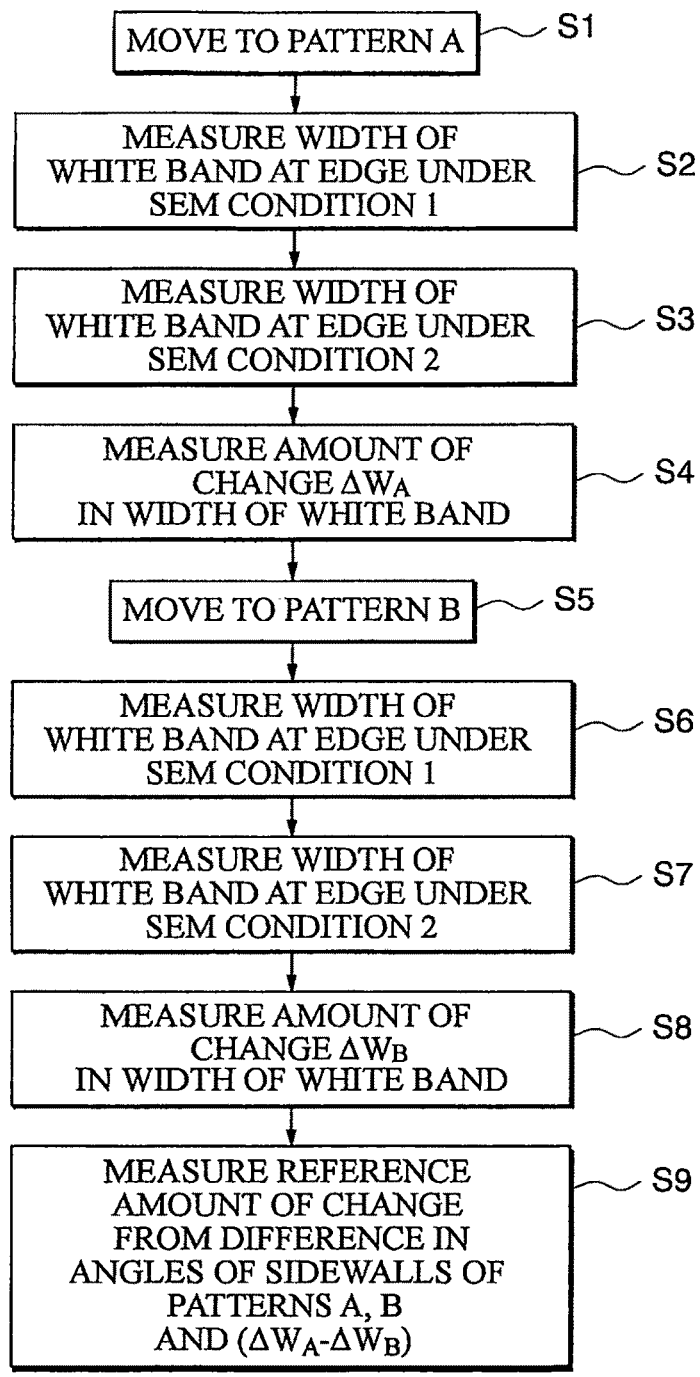
FIG. 1 is a flowchart of the calculation of a reference amount of change in a width of a white band according to a first embodiment.

S1: move to pattern A
S2: measure width of white band at edge of pattern A under SEM condition 1
S3: measure width of white band at edge of pattern A under SEM condition 2
S4: measure amount of change in width of white band of pattern A
S5: move to pattern B
S6: measure width of white band at edge of pattern B under SEM condition 1
S7: measure width of white band at edge of pattern B under SEM condition 2
S8: measure amount of change in width of white band of pattern B
S9: measure reference amount of change from difference in angles of sidewalls of patterns A, B and difference in amount of change in width of white band
S10: move to measurement pattern
S11: measure width of white band at edge of measurement pattern under SEM condition 1
S12: measure width of white band at edge of measurement pattern under SEM condition 2
S13: measure amount of change in width of white band in measurement pattern
S14: compare ΔW with reference amount of change
S15: cause stage or electron beam to be tilted at certain angle
S16: calculate angle of sidewall in measurement pattern from reference amount of change
S17: calculate angle of sidewall with tilt angle being corrected
S115: set number N of measurement points
S116: set width of measurement area
S117: repeat following procedure for measurement points 1 to N
S118: measure width of white band at edge under SEM condition 1
S119: set width of white band at edge under SEM condition 2
S120: calculate amount of change ΔW in width of white band
S121: calculate angle of sidewall of measurement areas from reference amount of change
S122: measurement of all measurement points completed
S123: calculate distribution of angle of sidewall

[Embodiments of the Invention]

(First Embodiment)

As will be described below, a microstructure inspection unit and a microstructure inspection method according to a first embodiment of the present invention calculate an angle of a sidewall of a microstructure pattern from a current value of an electron beam during taking of a SEM photograph and from a width of the white band in the SEM photograph.

Usually, when a microstructure pattern is observed under a CD-SEM, edge portion(s) of the microstructure pattern looks bright because a large number of secondary electrons are emitted therefrom. The edge portion(s) which looks bright will be referred to as white band(s) in this specification.

A width of the white band at the edge portion of the pattern becomes greater as a taper inclination of the pattern edge becomes less steep. It is therefore possible to estimate the angle of the sidewall to some extent from the thickness of the pattern and the width of the white band. However, it is known that the width of the white band will not change any more when the angle of the sidewall has a certain degree of steepness.

It is considered that, when the current value of the electron beam of the CD-SEM is changed, the amount of the secondary electrons emitted from the edge portion of the pattern might increase in proportion to the current value. It was found from our study that the width of the white band changes with the current value of the electron beam in accordance with the angles of the sidewalls of the pattern edge. The present invention uses this phenomenon. In addition to the width of the white band, signal intensity of the white band may also be used for the analysis.

Thus the microstructure inspection unit and the microstructure inspection method of the present invention can inspect the angle of the sidewall suitably even if the angle of the sidewall of the pattern to be measured is near 90 degrees.

After their intensive study, the present inventors found that the angle of the sidewall of the microstructure pattern has a correlation with the current value of the electron beam during taking of the SEM photograph and with the width of the white band in the SEM photograph. With this knowledge, it is possible to calculate the angle of the sidewall of the microstructure pattern by obtaining the current value of the electron beam during taking of the SEM photograph and the value of the width of the white band in the SEM photograph.

In this method, the angle of the sidewall of the microstructure pattern is calculated from the result of the taken SEM photograph. It is therefore possible to inspect the pattern to be measured in a non-destructive manner.

Since the angle of the sidewall is calculated through image processing of the SEM photograph, a multipoint measurement of the angle of the sidewall of the pattern to be measured is carried out easy. It is therefore possible to carry out the inspection with increased throughput as compared with the inspection using an AFM.

Hereinafter, the microstructure inspection unit of the present invention will be described specifically.

Figure 10:
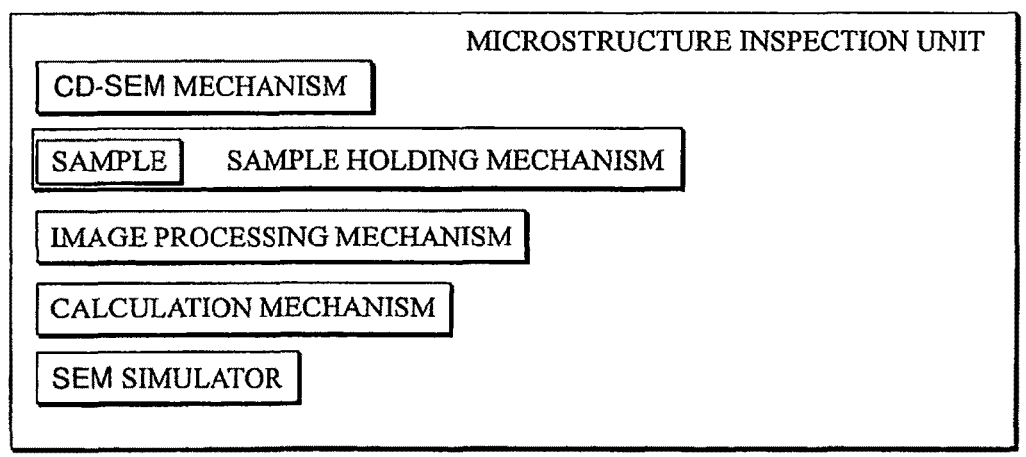
FIG. 10 is a schematic configuration diagram of a microstructure inspection unit according to an Example of the present invention.

For example, the microstructure inspection unit of the present invention has a structure illustrated in FIG. 10.

<Sample Holding Mechanism>

A sample holding mechanism fixes a sample provided with a pattern to be measured. The sample holding mechanism has a shape/function to suitably fix the sample in accordance with a shape/purpose of a structure in which the pattern to be measured is formed.

Preferably, the sample holding mechanism holds the sample in a manner such that the electron beam might be incident at an arbitrary angle with respect to the pattern to be measured during taking of the SEM photograph.

Since the sample holding mechanism holds the sample in a manner such that the electron beam and the pattern to be measured might be disposed at an arbitrary angle with respect to each other, it is possible to emit the electron beam at a position corresponding to the sidewall of the pattern to be measured and to obtain the SEM photograph with the white band even if the angle of the sidewall of the pattern to be measured is reversely tapered. Here, it suffices that the sample holding mechanism is a mechanism that holds the sample in a manner such that the electron beam and the pattern to be measured might be disposed at an arbitrary angle with respect to each other. In an actual apparatus, either of a stage on which the sample is fixed or the electron beam might be inclined (tilted).

With this configuration, the microstructure inspection unit of the present invention can measure the angle of the sidewall suitably even if the angle of the sidewall of the pattern to be measured is reversely tapered.

<CD-SEM Mechanism>

A CD-SEM mechanism takes a SEM photograph of the pattern to be measured.

In the CD-SEM, the electron beam emitted from an electron gun is converged by a condensing lens, made to pass through an aperture and to collide with the pattern to be measured. Secondary electrons emitted at this time are captured by a detector and are converted into electrical signals. Thus a two-dimensional image (i.e., a SEM photograph) is obtained.

<Image Processing Mechanism>

An image processing mechanism obtains the width of the white band at the edge portion of the pattern to be measured in the SEM photograph taken by the CD-SEM mechanism.

The width of the white band may be detected suitably by a well-known image processing technique. For example, since the white band looks brighter than the surrounding areas, the white band can be measured from the contrast in the SEM photograph.

<Calculation Mechanism>

A calculation mechanism calculates the angle of the sidewall of the pattern to be measured from the current value of the electron beam during taking of the SEM photograph and from the width of the white band described above.

After their intensive study, the present inventors found that the angle of the sidewall of the microstructure pattern has a correlation with the current value of the electron beam during taking of the SEM photograph and with the width of the white band in the SEM photograph. With this knowledge, it is possible to calculate the angle of the sidewall of the microstructure pattern by obtaining the current value of the electron beam during taking of the SEM photograph and the value of the width of the white band in the SEM photograph.

Preferably, the calculation mechanism has a function to calculate a reference amount of change by an SEM simulator. The reference amount of change is an amount of change in the width of the white band due to the change in the current value of the electron beam per unit angle.

Here, the SEM simulator is a software program for estimating the SEM image of the pattern or brightness distribution of the secondary electrons by calculating, by the Monte Carlo Method or other methods, behaviors of the secondary electrons emitted when the electron beams emitted from the electron gun of the CD-SEM collide with the pattern.

Of course, conditions of the electron beams (e.g., acceleration voltage and the current value) in the simulation can be changed arbitrarily. In addition, a material of the microstructure pattern can be selected arbitrarily and a three-dimensional configuration of the pattern can be designed arbitrarily. Thus the width of the white band can be measured from the image obtained by the SEM simulator or from the brightness distribution.

It is therefore possible to suitably grasp "a correlation among the angle of the sidewall of the microstructure pattern, the current value of the electron beam during taking of the SEM photograph, and the width of the white band in the SEM photograph."

Hereinafter, the microstructure inspection program and the microstructure inspection method of the present invention will be described specifically.

The microstructure inspection program and the microstructure inspection method of the present invention use the knowledge that "the angle of the sidewall of the microstructure pattern has a correlation with the current value of the electron beam during taking of the SEM photograph and with the width of the white band in the SEM photograph." The content of the present invention is not limited to the following embodiment.

<Calculating Reference Amount of Change>

First, a microstructure pattern of which an angle of the sidewall is known is measured. Then, a reference amount of change which is an amount of change in the width of the white band per unit angle is calculated from the amount of change in the width of the white band due to changes in the current value of the electron beam and the known angle of the sidewall.

In order to grasp "the correlation among the angle of the sidewall of the microstructure pattern, the current value of the electron beam during taking of the SEM photograph, and the width of the white band in the SEM photograph," the reference amount of change can be determined by measuring plural microstructure patterns of which angles of the sidewalls are known and performing a statistical procedure.

Specifically, the reference amount of change can be determined in the following manner: preparing microstructure patterns of which angles of the sidewalls are known; changing the current value of the electron beam during taking of the microstructure pattern by the CD-SEM; measuring the width of the white band at the edge portion of the microstructure pattern in the SEM photograph; and calculating the reference amount of change from the amount of change in the width of the white band due to changes in the current value of the electron beam and from the known angles of the sidewalls.

The reference amount of change may be calculated using a SEM simulator. Here, the SEM simulator is a software program for estimating the SEM image of the pattern or brightness distribution of the secondary electrons by calculating, by the Monte Carlo Method or other methods, behaviors of the secondary electrons emitted when the electron beams emitted from the electron gun of the CD-SEM collide with the pattern.

Of course, conditions of the electron beams (e.g., acceleration voltage and the current value) in the simulation can be changed arbitrarily. In addition, a material of the pattern can be selected arbitrarily and a three-dimensional configuration of the pattern can be designed arbitrarily. Thus the width of the white band can be measured from the image obtained by the SEM simulator or from the brightness distribution.

Hereinafter, as an example, a calculation of the reference amount of change will be described with reference to a case in which two samples different in the angles of the sidewalls are prepared and two conditions with different current values of the electron beams are provided.

First, two patterns (hereinafter, referred to as "pattern A" and "pattern B") with different angles of the sidewalls are formed from the same material (e.g., resist or chromium) as those of the samples of which angles of the sidewall will be measured. Angles of the sidewalls of the pattern A and the pattern B are previously measured using a cross-sectional SEM, an AFM (atomic force microscope) or other devices. Preferably, the values of the angles of the sidewalls of the pattern A and the pattern B differ from each other as much as possible. For example, one of the patterns A and B is preferably almost upright and the other is preferably tapered at about 70 degrees.

Next, two conditions (hereinafter, referred to as a "SEM condition 1" and a "SEM condition 2") with different current values of the electron beams are provided as measuring conditions in the CD-SEM.

FIG. 1 is a flowchart of the calculation procedure of the reference amount of change in the width of the white band per 1 degree of the angle of the sidewall. The dimension of the reference amount of change in this example is [length/angle].

First, the CD-SEM mechanism is moved to the pattern A (S1) and the width of the white band at the edge is measured under the SEM condition 1 (S2). Next, the width of the white band at the edge is measured under the SEM condition 2 (S3). The amount of change $\Delta W_A$ of the width of the white band is calculated from the results of S2 and S3 (S4).

Next, the CD-SEM mechanism is moved to the pattern B (S5) and the width of the white band at the edge is measured under the SEM condition 1 (S6). Next, the width of the white band at the edge is measured under the SEM condition 2 (S7). The amount of change $\Delta W_B$ of the width of the white band is calculated from the results of S6 and S7 (S8).

Finally, the reference amount of change is calculated (S9) from the difference in the angles of the sidewalls of the patterns A and B and from $\Delta W_A - \Delta W_B$ with the following formula:

$$|\Delta W_A - \Delta W_B|/|(\text{Angle of sidewall of microstructure pattern A})-(\text{Angle of sidewall of microstructure pattern B})|=(\text{Reference amount of change}).$$

Note that, when the SEM simulator is used, all of the preparation of the samples used for the calculation of the reference amount of change and all of the measurement of the width of the white band under the SEM condition 1 and the SEM condition 2 may be conducted on a computer.

<Obtaining Amount of Change>

Next, a pattern to be measured of which an angle of the sidewall is not known is prepared and the current values of the electron beams during taking of the microstructure pattern by the CD-SEM are changed (SEM condition 1 and SEM condition 2). Then, the width of the white band at the edge portion of the microstructure pattern in the SEM photograph is measured and the amount of change in the width of the white band due to changes in the current values of the electron beams is obtained.

<Calculating Angle of Sidewall of Pattern to be Measured>

Next, the angle of the sidewall of the pattern to be measured in the pattern to be measured of which angle of the sidewall is not known is calculated from the amount of change in the width of the white band due to changes in the current values of the electron beams and from the reference amount of change.

The angle of the sidewall of the pattern to be measured may be calculated in accordance with the method of calculating the reference amount of change.

With the method described above, the angle of the sidewall of the pattern to be measured can be measured using the CD-SEM.

EXAMPLES

Hereinafter, as an example, a calculation of the angle of the sidewall of the pattern to be measured will be described with reference to a case in which two samples different in the angles of the sidewalls are prepared and two conditions with different current values of the electron beams are provided. Note that the example described below may also be applied to a case in which the angle of the sidewall of the pattern to be measured is reversely tapered.

Figure 2:
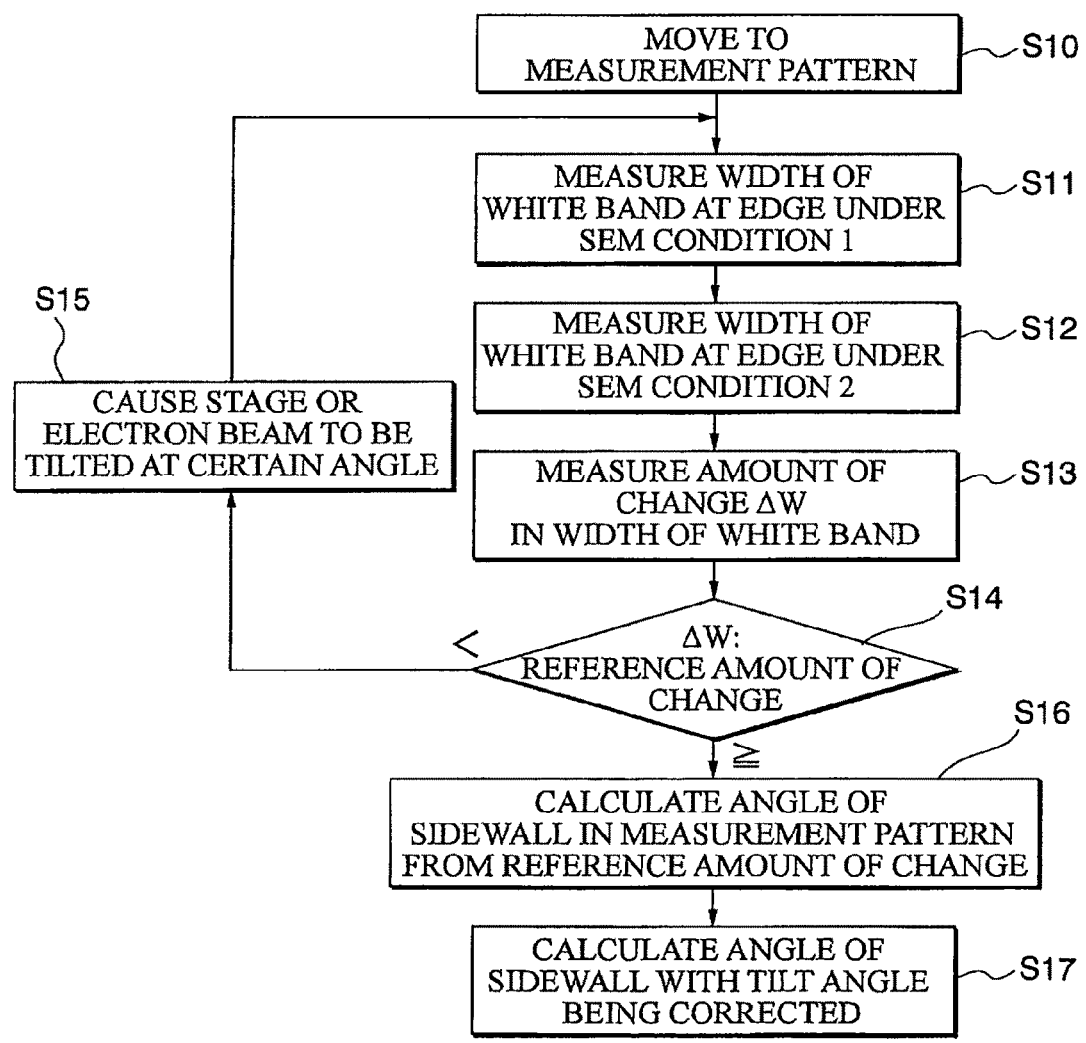
FIG. 2 is a flowchart of the measurement of an angle of a sidewall of a pattern to be measured.

FIG. 2 is a flowchart of a measurement procedure for the angle of the sidewall of the pattern to be measured (this procedure may also be applied to a case in which the angle of the sidewall of the pattern to be measured is reversely tapered).

First, the CD-SEM mechanism is moved to the measurement pattern of which angle of the sidewall is not known (S10) and the width of the white band of the edge is measured under the SEM condition 1 (S11). Next, the width of the white band of the edge is measured under the SEM condition 2 (S12). The amount of change $\Delta W$ of the width of the white band is calculated from the results of S11 and S12 (S13). Next, this $\Delta W$ is compared with the reference amount of change (S14). If $\Delta W$ is smaller than the reference amount of change, it is considered that the sidewall of the measurement pattern is reversely tapered. In this case, the stage or the beam is tilted at a certain angle (S15) and the routine returns to S11. If $\Delta W$ is equal to or larger than the reference amount of change in S14, the angle of the sidewall of the measurement pattern is calculated from the reference amount of change, the angle of the sidewall of pattern A (or pattern B), and the amount of change in the width of the white band (S16). Finally, if the stage or the beam has been tilted, the angle of the sidewall is calculated with the tilt angle being corrected (S17). A formula for the calculation of the angle of the sidewall of an arbitrary pattern is given below. Note that, if the stage or the beam was not tilted, a correction amount for the tilt angle is 0 degrees.

Note that, if no pattern which is reversely tapered is dealt with, S15 and a tilting mechanism may be omitted.

(Angle of sidewall of pattern to be measured)=[(Tilt angle)+(Angle of sidewall of pattern A)+($\Delta W_A - \Delta W$)/(Reference amount of change)

$\Delta W_A$: amount of change in the width of the white band of the pattern A

ΔW: amount of change in the width of the white band of the pattern to be measured Example 1

Hereinafter, specific Examples about the use of the microstructure inspection unit of the present invention will be described.

<Calculation of Reference Amount of Variation>

In order to calculate the reference amount of variation per 1 degree of the angle of the sidewall, two Space patterns on a photomask were prepared. The angle of the sidewall of each pattern was already measured using the AFM. A left edge of the pattern A was 87 degrees and a left edge of the pattern B was 78 degrees.

Measuring conditions of the CD-SEM were defined as follows.

SEM condition 1: beam current was 5 pA
SEM condition 2: beam current of was 10 pA First, the CD-SEM mechanism is moved to the pattern A and an image is obtained under the SEM condition 1. Then, the width of the white band was measured. The width of the white band was 19.9 nm.

Next, in the same pattern A, an image is obtained under the SEM condition 2. Then, the width of the white band was measured. The width of the white band was 21.0 nm.

Thus the amount of change in the width of the white band under the SEM conditions is 1.1 nm.

Next, the CD-SEM mechanism was moved to the pattern B, an image was obtained under the SEM condition 1 and the width of the white band was measured to be 25.7 nm.

Next, in the same pattern, an image was obtained under the SEM condition 2 and the width of the white band was measured to be 29.7 nm.

Thus the amount of change in the width of the white band under the SEM conditions is 4.0 nm.

Figure 3:
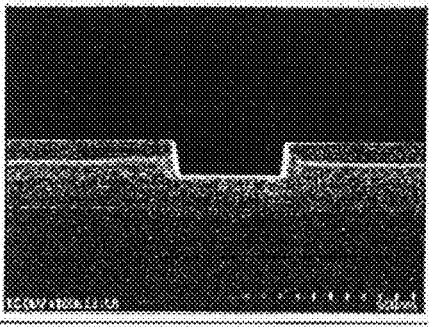
FIG. 3 illustrates SEM images representing Example 1 and measurement results of widths of white bands.
Figure 3:
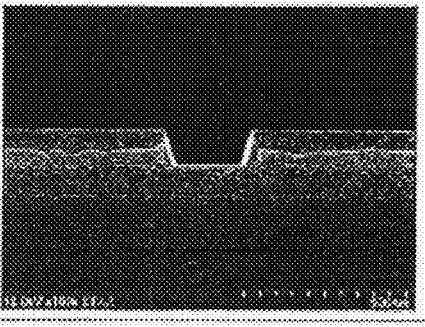
Figure 3:
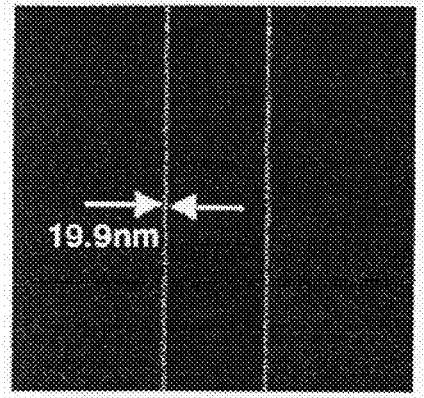
Figure 3:
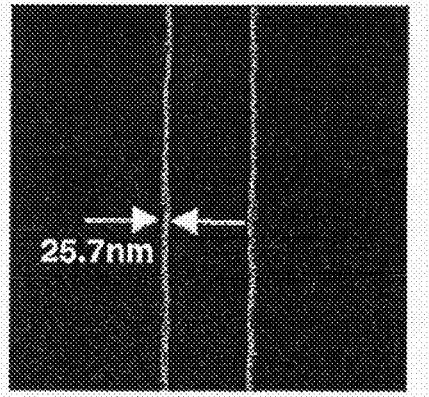
Figure 3:
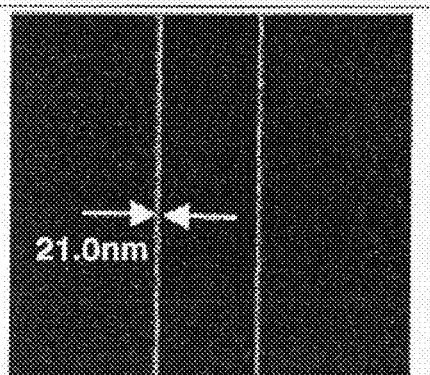
Figure 3:
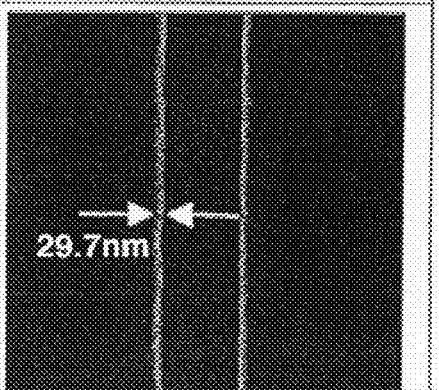

Pattern images of the pattern A and the pattern B under each of the SEM conditions are illustrated in FIG. 3.

Figure 4:
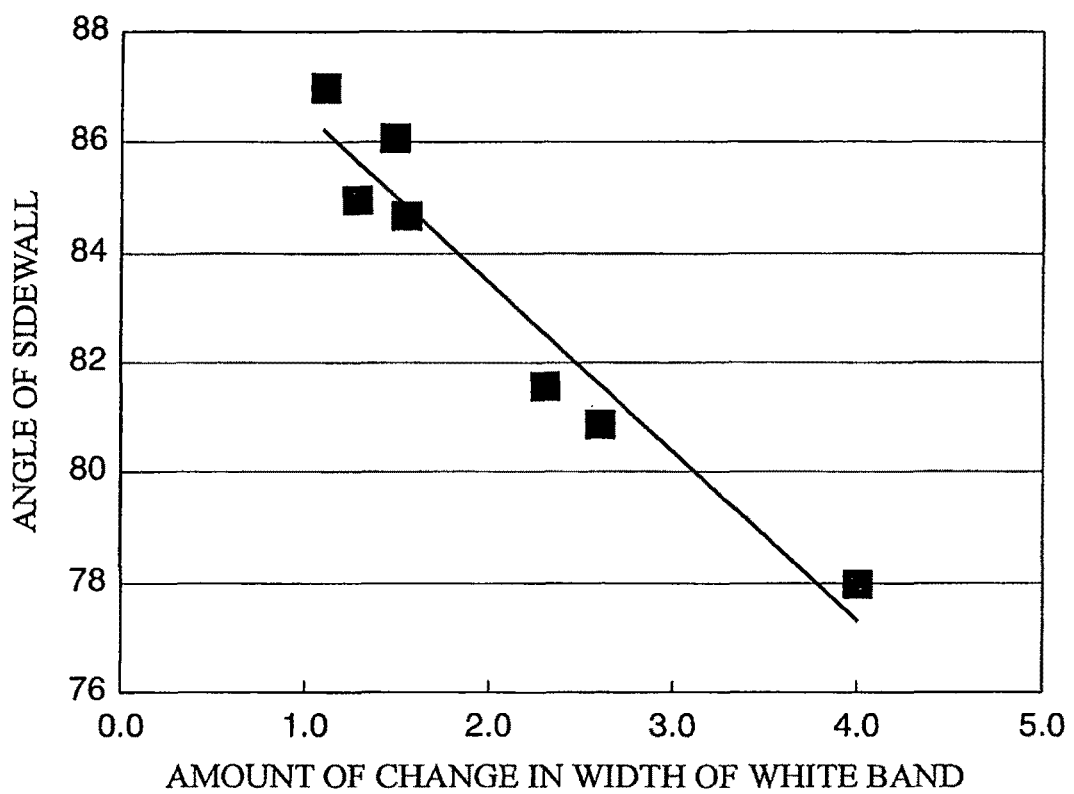
FIG. 4 is a graph illustrating a relationship between an amount of variation in the width of the white band and the angle of the sidewall.
Figure 5:
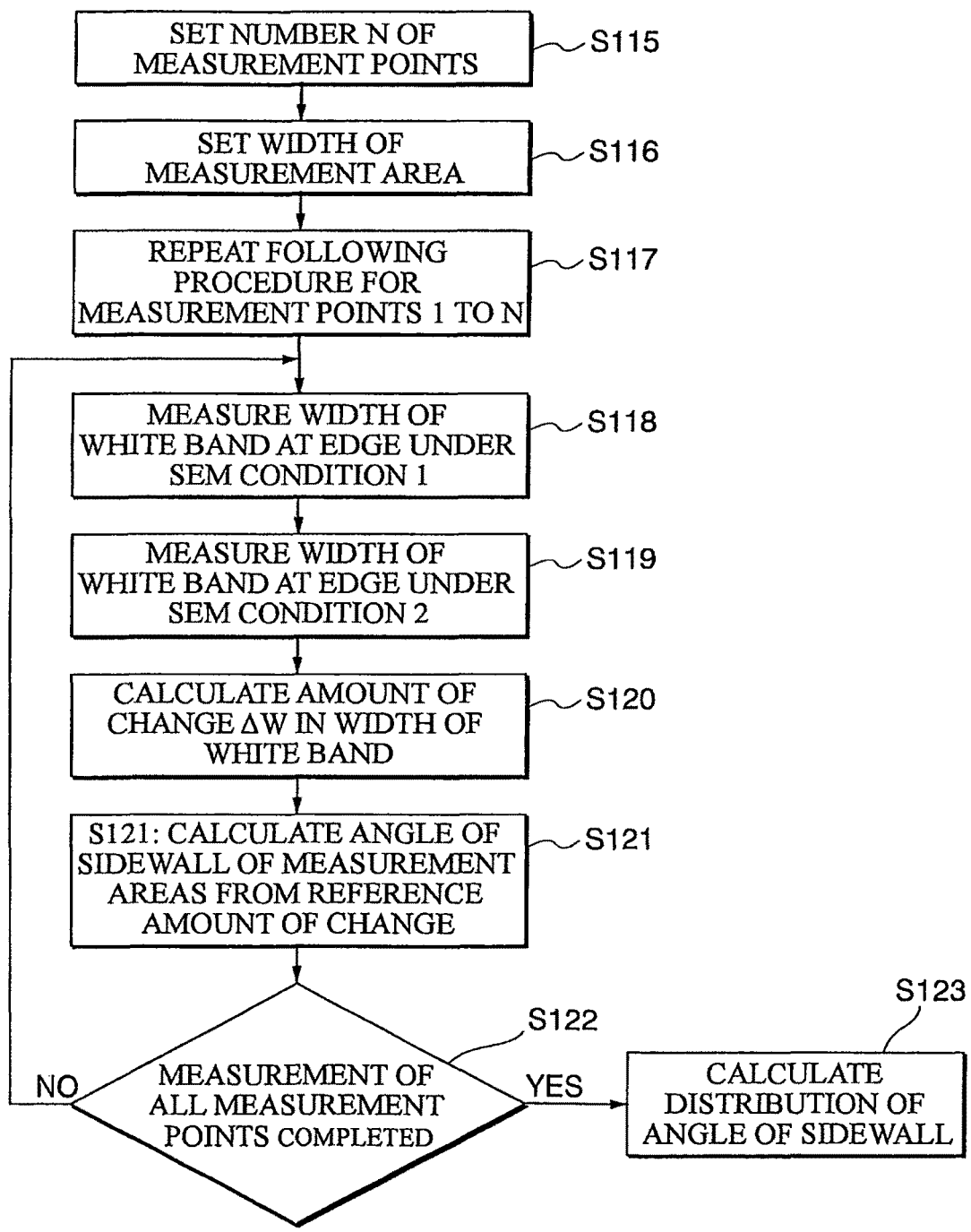
FIG. 5 is a flowchart of a calculation procedure of distribution of an angle of a sidewall of a pattern to be measured according to a second embodiment.

A graph of a relationship between the amount of change in the white band and the angle of the sidewall is illustrated in FIG. 4.

Measurement results on seven patterns in total including the patterns A and B measured by the above-described measuring method are illustrated in FIG. 4. FIG. 4 is a graph in which the angle of the sidewall of each pattern previously measured using the AFM and the amount of change in the white band are plotted. With the plot, primary linear approximation about a correlation between the angle of the sidewall and the amount of change in the white band was obtained. As a result, a square value of a correlation coefficient R was 0.94, which represents a close correlation.

The reference amount of change per 1 degree of the angle of the sidewall was defined to be 0.32 [nm/angle] from the difference in the angles of the sidewalls (87 degrees–78 degrees=9 degrees) and the difference in the amount of change in the width of the white band of the patterns A and B (4.0–1.1=2.9 nm).

<Calculation of Angle of Sidewall of Pattern to be Measured>

Next, the CD-SEM mechanism was moved to a pattern of which an angle of the sidewall is not known which is an actual object to be measured, an image was obtained under the SEM condition 1 and the SEM condition 2, and the width of the white band was measured. As a result, the width of the white band was 19.7 nm under the SEM condition 1 and 21.5 nm under the SEM condition 2. Thus the amount of change was 1.8 nm.

Next, the angle of the sidewall was calculated with the following formula.

(Angle of sidewall of pattern to be measured)=(Angle of sidewall of pattern B)+($\Delta W_B - \Delta W$)/(Reference amount of change)

$\Delta W_B$: amount of change in the width of the white band of the pattern B

ΔW: amount of change in the width of the white band of the pattern to be measured Thus the angle of the sidewall of the pattern to be measured was 78 degrees+(4.0–1.8)/0.32=84.9 degrees.

Note that the angle of the sidewall of this pattern was measured using the AFM to be 85 degrees, which was substantially in agreement with the measurement result of the method of the present invention.

<Calculation of Angle of Sidewall of Pattern to be Measured (When Angle of Sidewall is Reversely Tapered)>

Next, the CD-SEM mechanism was moved to a pattern of which an angle of the sidewall is not known, images were obtained under the SEM conditions 1 and 2 and the width of the white bands were measured. As a result, the width of the white band was 19.2 nm under the SEM condition 1 and 19.3 nm under the SEM condition 2. It was found that the amount of change in the width of the white band was as small as 0.1 nm, which was smaller than the reference amount of change (0.32 nm). It is therefore considered that this sidewall is reversely tapered.

Then, the stage on which the pattern is mounted was tilted by 5 degrees. The width of the white band was measured again under each SEM condition and was 19.4 nm under the SEM condition 1 and 20.3 nm under the SEM condition 2. The amount of change was 0.9 nm this time, which is larger than the reference amount of change.

Next, the angle of the sidewall was calculated with the following formula.

(Angle of sidewall of pattern to be measured)=[(Tilt angle)+(Angle of sidewall of pattern B)+($\Delta W_B - \Delta W$)]/(Reference amount of change)

$\Delta W_B$: amount of change in the width of the white band of the pattern B

ΔW: amount of change in the width of the white band of the pattern to be measured Thus the angle of the sidewall of the pattern to be measured was 5 degrees+78 degrees+(4.0–0.9)/0.32=92.7 degrees.

As described above, it was possible to obtain the angle of the sidewall even when the angle of the sidewall was reversely tapered over 90 degrees.

(Second Embodiment)

Hereinafter, a second embodiment of the measuring method of the present invention will be described. A description on members and processes common to those of the first embodiment will be omitted. Different members and processes will be described in detail.

In the microstructure inspection method according to the present embodiment, in the calculating the angle of the sidewall of the pattern to be measured from the amount of change in the width of the white band due to changes in the current value of the electron beam in the pattern to be measured of which an angle of the sidewall is not known and from the reference amount of change, measurement points are set on the white band, measurement distance corresponding to the distance from the measurement points is determined and white band sections within the measurement distance are defined as measurement areas.

If the pattern to be measured has great edge roughness, it is considered that the angle of the sidewall varies from area to area.

Since the measurement points are set on the white band and the measurement areas are divided within the measurement distance corresponding to the distance from the measurement points, the angle of the sidewall can be calculated for each measurement area defined for each measurement point. Thus, the angle of the sidewall is calculated for each measurement point even if the angle of the sidewall varies from area to area of the pattern to be measured, and therefore distribution of variation in the angle of the sidewall can be obtained.

At this time, the measurement areas can be defined at arbitrary parts of the pattern to be measured by controlling the number of the measurement points and the width of the measurement areas.

Hereinafter, as an example, an embodiment will be described in which the measurement points are set and the distribution of the angle of the sidewall of the pattern to be measured is obtained in the calculation of the angle of the sidewall of the pattern to be measured will be described with reference to a case in which two samples different in the angles of the sidewalls are prepared and two conditions with different current values of the electron beams are provided.

FIG. 3 is a flowchart of a calculation procedure of the distribution of the angle of the sidewall of the pattern to be measured.

For the evaluation of the angle of the sidewall of a pattern with great edge roughness, the number N of the points at which the angle of the sidewall is measured is set first (S115). Next, the width of the measurement area at each measurement point is determined (S116). Here, the width of the measurement area is determined so as not to overlap the measurement areas at neighboring measurement points. The following procedure is carried out for all the measurement points. The width of the white band at the edge is measured under the SEM condition 1 (S118) and then the width of the white band at the edge is measured under the SEM condition 2 (S119). The amount of change ΔW in the width of the white band is calculated (S120). The angle of the sidewall of the measurement area is calculated from the reference amount of change (S121). After the measurement of all the measurement points is completed (S122), the distribution of the angle of the sidewall is calculated from the obtained data (S123).

Example 2

<Calculation of Angle of Sidewall Distribution>

The measurement points were set and the distribution of the angle of the sidewall of the pattern to be measured was obtained.

The number of the measurement points of the angle of the sidewall was set to 5 for one of the edges. The width of the measurement area at each of the measurement points was set to 50 pixels. As in Example 1, the width of the white band at the edge of each measurement area was measured under the SEM condition 1 and the SEM condition 2, and the amount of change ΔW in the width of the white band was calculated. The angle of the sidewall in each measurement point was calculated from the reference amount of change and the distribution of the angle was evaluated.

The above-described measurement was carried out for each of the normal straight line pattern and a pattern with great roughness.

Figure 6A:
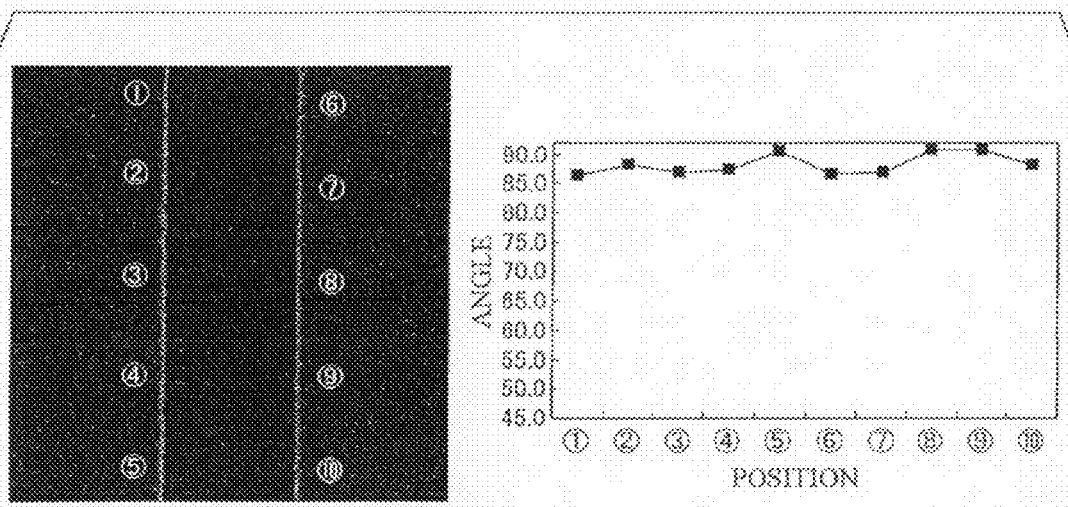
FIG. 6A illustrates a SEM image representing a normal straight line pattern of Example 2 and the distribution of the angle of the sidewall.
Figure 6B:
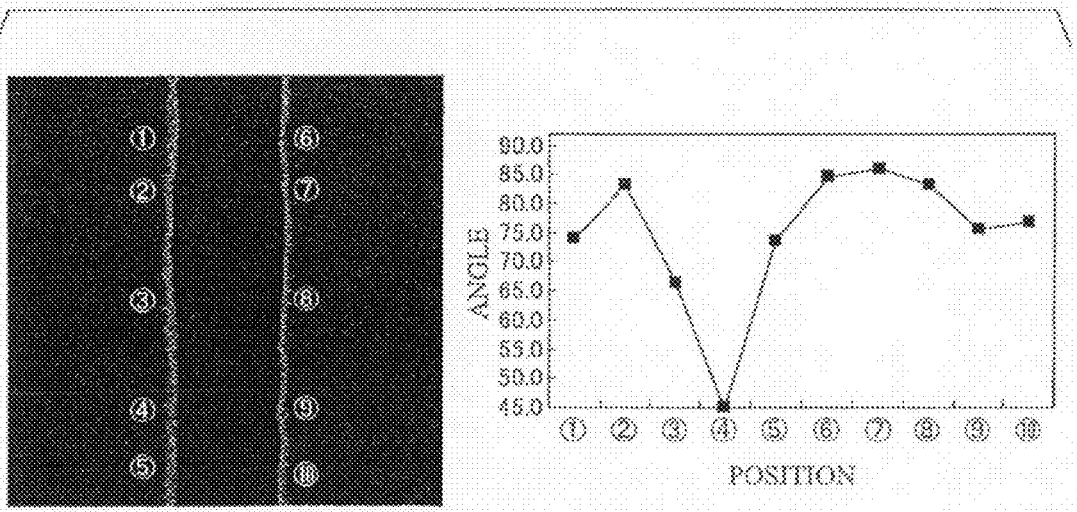
FIG. 6B illustrates a SEM image representing a pattern with greater roughness of Example 2 and the distribution of the angle of the sidewall.

The distribution of the angle of the sidewall of the pattern is illustrated in FIGS. 6A and B. The normal straight line pattern is illustrated in FIG. 6A and the pattern with great roughness is illustrated in FIG. 6B.

FIGS. 6A and B show that the angle of the sidewall is stable at 86 to 90 degrees in the straight line pattern and the angle of the sidewall changes from 45 to 85 degrees from area to area in the pattern with great roughness.

It was therefore possible to obtain the distribution of change in the angle of the sidewall by setting the measurement points.

(Third Embodiment)

Hereinafter, a third embodiment of the measuring method of the present invention will be described.

In the first and second embodiments described above, two SEM conditions, i.e., the SEM condition 1 and the SEM condition 2, were provided. The difference between these two SEM conditions is in the current value of the electron beam. Under these two conditions, the amount of change in the width of the white band was measured and the angle of the sidewall was calculated from the measurement result.

In the third embodiment, the SEM condition 1 and the SEM condition 2 are the same in the current value of the electron beam but, instead, different in an amplification value of a photo-multiplier tube in a secondary electron detector. Under these two (or more) SEM conditions, the amount of change in the width of each white band is measured and the angle of the sidewall is calculated from the measurement result.

Next, the amplification value of the photo-multiplier tube in the secondary electron detector will be described specifically. The SEM captures the secondary electrons emitted from the sample by a detector, converts the captured secondary electrons into light signals by a scintillator, and converts and amplifies the light signals into electrical signals using the photo-multiplier tube to form an image. The amplification value is a parameter of the photo-multiplier tube, which affects the contrast of the SEM photograph image.

Usually, when a microstructure pattern is observed under a CD-SEM, edge portion(s) of the microstructure pattern looks bright because a large number of secondary electrons are emitted therefrom. The edge portion(s) which looks bright will be referred to as white band(s) in this specification.

A width of the white band of the edge portion of the pattern becomes greater as a taper inclination of the pattern edge becomes less steep. It is therefore possible to estimate the angle of the sidewall to some extent from the thickness of the pattern and the width of the white band. However, it is known that the width of the white band will not change any more when the angle of the sidewall has a certain degree of steepness.

It is considered, however, that areas which look bright at the pattern edge portions increase in size as a result of an increase in the number of the signals converted into the electrical signals in proportion to the amplification value when the amplification value of the CD-SEM is changed. This is considered to be because the distribution of the secondary electrons emitted from the object is affected by very small bumps near a surface of the microstructure, sensitivity of the detector to the secondary electrons in the SEM photograph is changed due to the change in the amplification value of the photo-multiplier tube, and the width of the white band has been changed due to varying sharpness in the contrast of the SEM photograph.

It was found from our study that the width of the white band changes due to the change in the amplification value in accordance with the angle of the sidewalls of the pattern edge. The present embodiment uses this phenomenon.

Accordingly, with the microstructure inspection method of the present invention, the angle of the sidewall of the pattern to be measured as large as about 90 degrees, not smaller than 70 degrees and more specifically not smaller than 80 degrees, can be inspected suitably.

As described above, the angle of the sidewall can be inspected by measuring the amount of variation in the width of the white band under two (or more) SEM conditions with different amplification values of the photo-multiplier tube in the secondary electron detector. Here, when the amplification value of the photo-multiplier tube is changed by different widths between the SEM conditions, a different amount of variation in the width of the white band due to the change in the amplification value is obtained. FIG. 10 illustrates this phenomenon.

In experiments with four experimental lines illustrated in FIG. 10, the amount of variation in the width of the white band was measured under two SEM conditions for each line. In a first experimental line, variation in the amplification value of the photo-multiplier tube under the two SEM conditions was set to between 42 and 40 (C42-40). Similarly, in second to fourth experimental lines, variation in the amplification value was set to between 46 and 40 (C46-40), 50 and 40 (C50-40), and 54 and 40 (C54-40), respectively. Accordingly, the width of change in the amplification value of the photo-multiplier tube in the first to fourth experimental lines is 2, 6, 10 and 14, respectively. Under these conditions, the amount of variation in the width of the white band was measured using plural kinds of patterns. As a result, in the first and second experimental lines, no significant variation was observed in the width of the white band during the inspection of the patterns with the angle of the sidewall of about 75 to 88 degrees. However, in the third experimental line, noticeable variation was observed in the width of the white band. In the fourth experimental line, more significant variation was observed in the width of the white band. It is therefore preferable to perform the inspection with varying amplification values of the photo-multiplier tubes.

After their intensive study, the present inventors found that the angle of the sidewall of the microstructure pattern has a correlation with the amplification value described above during taking of the SEM photograph and with the width of the white band in the SEM photograph. With this knowledge, it is possible to calculate the angle of the sidewall of the microstructure pattern by obtaining the amplification value during taking of the SEM photograph and the value of the width of the white band in the SEM photograph.

Here, since the angle of the sidewall of the microstructure pattern is calculated by taking the SEM photograph, the pattern to be measured can be inspected in an un-destructive manner.

Since the angle of the sidewall is calculated through image processing of the SEM photograph, a multipoint measurement of the angle of the sidewall of the pattern to be measured is carried out easy. It is therefore possible to carry out the inspection with increased throughput as compared with an inspection using an AFM.

The microstructure inspection method of the present embodiment is performed in a similar manner to that of the microstructure inspection method according to the above-described first embodiment, except that the SEM condition 1 and the SEM condition 2 are provided differently.

The microstructure inspection method of the present embodiment uses the knowledge that "the angle of the sidewall of the microstructure pattern has a correlation with the amplification value during taking of the SEM photograph and with the width of the white band of the SEM photograph." Accordingly, the inspection method is not limited to the above-described embodiments.

In the present embodiments described above, plural SEM photographs were taken using various photo-multiplier tubes. Alternatively, however, the plural SEM photographs may be taken with varying measurement parameters other than the amplification value. If the change in the width of the white band due to the change in the measurement parameter can be observed, the correlative change can be used for the calculation of the angle of the sidewall.

Example 3

Hereinafter, a specific Example about the method of measuring the angle of the sidewall of the present embodiment will be described.

<Calculation of Reference Amount of Variation>

In order to calculate the reference amount of variation per 1 degree of the angle of the sidewall, two Space patterns on a photomask were prepared. The angle of the sidewall of each pattern was already measured using the AFM. A left edge of the pattern A was 87 degrees and a left edge of the pattern B was 78 degrees.

Two CD-SEM measuring conditions were provided: the SEM condition 1 and the SEM condition 2. The amplification value was larger in the SEM condition 1 than in the SEM condition 2.

In this Example, a SEM device (product number: LWM9000SEM manufactured by Vistec Semiconductor Systems Inc.) was used. The amplification value of the photo-multiplier tube was set to 40 for the SEM condition 1 in the above-described device and the amplification value of the photo-multiplier tube was set to 60 for the SEM condition 2.

First, the SEM device was moved to the pattern A, an image was obtained under the SEM condition 1 and the width of the white band was measured to be 18.1 nm.

Next, in the same pattern A, an image was obtained under the SEM condition 2 and the width of the white band was measured to be 18.7 nm.

Thus the amount of change in the width of the white band under the SEM conditions is 0.6 nm.

Next, the SEM device was moved to the pattern B, an image was obtained under the SEM condition 1 and the width of the white band was measured to be 25.7 nm.

Next, in the same pattern, an image was obtained under the SEM condition 2 and the width of the white band was measured to be 28.9 nm.

Thus the amount of change in the width of the white band under the SEM conditions is 3.2 nm.

Pattern images of the pattern A and the pattern B under each of the SEM conditions are illustrated in FIG. 7.

Figure 8:
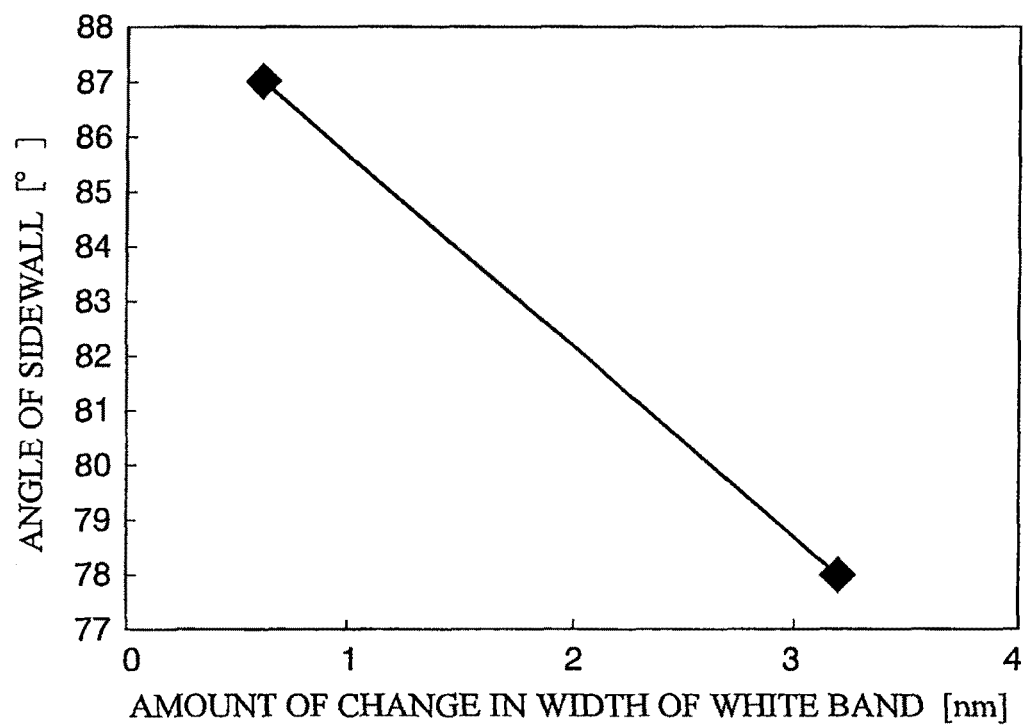
FIG. 8 is a graph illustrating a relationship between an amount of variation in the width of the white band and an angle of the sidewall in the Example described above.
Figure 9:
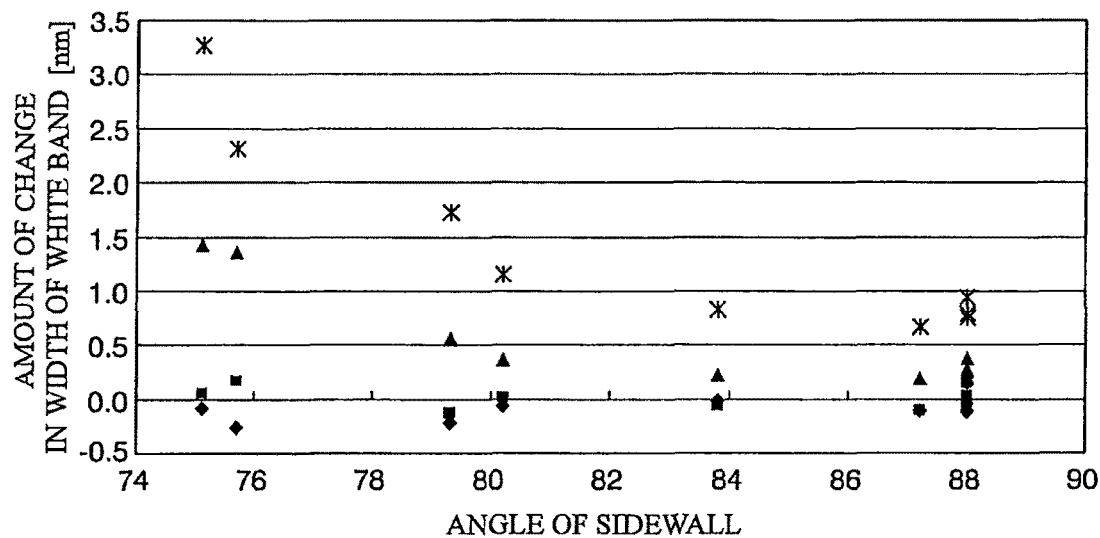
FIG. 9 is a graph illustrating a relationship between an amount of variation in the width of the white band and the angle of the sidewall when an amplification value of a photomultiplier tube is changed at varying widths of change.

A graph of a relationship between the amount of change in the white band and the angle of the sidewall is illustrated in FIG. 8.

The reference amount of change per 1 degree of the angle of the sidewall was defined to be 0.29 [nm/angle] from the difference in the angles of the sidewalls (87 degrees−78 degrees=9 degrees) and the difference of the amount of change in the width of the white band of the patterns A and B (3.2−0.6=2.6 nm).

<Calculation of Angle of Sidewall of Pattern to be Measured>

Next, the SEM device was moved to a pattern of which an angle of the sidewall is not known which is an actual object to be measured, an image was obtained under the SEM condition 1 and the SEM condition 2, and the width of the white band was measured. As a result, the width of the white band was 20.6 nm under the SEM condition 1 and 22.9 nm under the SEM condition 2. Thus the amount of change was 2.3 nm.

Next, the angle of the sidewall was calculated with the following formula.

(Angle of sidewall of pattern to be measured)=(Angle of sidewall of pattern B)+($\Delta W_B$−$\Delta W$)/(Reference amount of change)

$\Delta W_B$: amount of change in the width of the white band of the pattern B $\Delta W$: amount of change in the width of the white band of the pattern to be measured Thus the angle of the sidewall of the pattern to be measured was 78 degrees+(3.2−2.3)/0.29=81.1 degrees.

Note that the angle of the sidewall of this pattern was measured using the AFM to be 81.2 degrees, which was substantially in agreement with the measurement result of the method of the present embodiment.

Note that a computer program for implementing the functions of the microstructure inspection according to each embodiment of the present invention may be developed. Such a program may be recorded on a computer-readable recording medium. The functions of the microstructure inspection may be performed through the execution of the above-described program in a computer system.

The above-described computer system includes an operation system and hardware necessary for the execution. Examples of the above-described recording medium include a magnetic disk, a hard disk, a magneto-optical disc and a CD-ROM.

[Industrial Applicability]

The microstructure inspection unit and the microstructure inspection method according to an aspect of the present invention are characterized by taking SEM photographs under plural SEM conditions and calculating an angle of a sidewall of a microstructure pattern from a width of a white band in the SEM photographs. It is therefore possible in microstructures of various shapes to measure the angle of the sidewall at an edge portion of a pattern in a highly precise and non-destructive manner with high throughput.

The invention claimed is:

1. A microstructure inspection method which inspects an angle of a sidewall of a microstructure pattern, the method comprising:
   obtaining scanning electron microscope (SEM) images of a sample microstructure pattern having a sidewall of which angle is unknown and plural reference microstructure patterns having sidewalls of which angles are known and are different from each other under plural SEM conditions having mutually different current values of electron beams or mutually different amplification values of photo-multiplier tubes;
   measuring a white band-width variation of each of the sample microstructure pattern and the plural reference microstructure patterns, the white-band width variation being an amount of change of a width of a white band at an edge portion of the microstructure pattern in the SEM image when the current value of the electron beam is changed or the amplification value of the photo-multiplier tube is changed;
   obtaining a correlation between an angle of a sidewall of a microstructure pattern and a white band-width variation, by using the measurement results of the white band-width variations of the plural reference microstructure patterns; and
   calculating the angle of the sidewall of the sample microstructure pattern, by using the correlation and the measurement result of the white band-width variation of the sample microstructure pattern.

2. The microstructure inspection method according to claim 1, further comprising:
   causing, if the white band-width variation of the microstructure pattern in the SEM image is less than a predetermined value, the electron beam and a sample provided with the microstructure pattern to be tilted relative to each other by a tilt angle with which the white band-width variation of the microstructure pattern is equal to or greater than the predetermined value; and
   correcting the calculated angle of the sidewall of the sample microstructure pattern corresponding to an amount of the tilt angle.

3. The microstructure inspection method according to claim 1, further comprising:
   obtaining SEM images of a first reference microstructure pattern under a first and a second SEM conditions, measuring a width of a white band at an edge portion of the first reference microstructure pattern in the SEM image, and calculating a first difference $\Delta W_A$ between the widths of the white band of the first reference microstructure pattern under the first and the second SEM conditions;
   obtaining SEM images of a second reference microstructure pattern under the first and the second SEM conditions, measuring a width of a white band at an edge portion of the second reference microstructure pattern in the SEM image, and calculating a second difference $\Delta W_B$ between the widths of the white band of the second reference microstructure pattern under the first and the second SEM conditions; and
   calculating a reference white band-width variation with the following formula (A), (Reference white band-width variation)=|$\Delta W_A$−$\Delta W_B$|/|(Angle of first reference sidewall of microstructure pattern)−(Angle of sidewall of second reference microstructure pattern)|  (formula (A)).

4. The microstructure inspection method according to claim 3, further comprising:
   obtaining SEM images of a sample microstructure pattern under the first and the second SEM conditions, measuring a width of a white band at an edge portion of the sample microstructure pattern in the SEM image, and calculating a third difference $\Delta W$ between the widths of the white band of the sample microstructure pattern under the first and the second SEM conditions; and
   calculating the angle of the sidewall of the sample microstructure pattern with the following formula (B) using the reference white band-width variation, the angle of the sidewall of the pattern, the second difference $\Delta W B$, and the third difference $\Delta W$:

(Angle of sidewall of sample microstructure pattern)= (Angle of sidewall of second reference microstructure pattern)+($\Delta W_B$−$\Delta W$/(Reference white band-width variation)  (formula (B)).

5. The microstructure inspection method according to claim 1, wherein while obtaining the SEM images of the microstructure pattern, a measurement area having a predetermined width is defined along a longitudinal direction of the white band, and distribution of the width of the white band in the measurement area is measured.

6. A microstructure inspection unit which inspects an angle of a sidewall of a microstructure pattern, the unit comprising:
   a sample holding mechanism which fixes a sample provided with a microstructure pattern to be measured;
   a critical dimension scanning electron microscope (CD-SEM) mechanism which obtains SEM images of the microstructure pattern under plural SEM conditions having mutually different current values of electron beams or mutually different amplification values of photo-multiplier tubes;

an image processing mechanism which obtains a width of a white band at an edge portion of the microstructure pattern from the SEM images; and a calculation mechanism which calculates an angle of a sidewall of a sample microstructure pattern, wherein the image processing mechanism measures a white band-width variation of each of the sample microstructure pattern having a sidewall of which angle is unknown and plural reference microstructure patterns having sidewalls of which angles are known and are different to each other, the white-band width variation being an amount of change of a width of a white band at an edge portion of the microstructure pattern in the SEM image when the current value of the electron beam is changed or the amplification value of the photo-multiplier tube is changed, the calculation mechanism obtains a correlation between an angle of a sidewall of a microstructure pattern and a white band-width variation, by using the measurement results of the white band-width variations of the plural reference microstructure patterns, and the calculation mechanism calculates the angle of the sidewall of the sample microstructure pattern, by using the correlation and the measurement result of the white band-width variation of the sample microstructure pattern.

7. The microstructure inspection unit according to claim 6, wherein the sample holding mechanism holds the sample in a manner such that a relative angle of incidence of the electron beam is changeable with respect to the pattern to be measured during the obtaining of the SEM image.

8. The microstructure inspection unit according to claim 6, wherein the calculation mechanism further includes a SEM simulator that simulates the white band-width variation.

9. A non-transitory computer-readable storage medium storing a microstructure inspection program which, when executed by a computer, inspects an angle of a sidewall of a microstructure pattern, by performing:

a routine which obtains scanning electron microscope (SEM) images of a sample microstructure pattern having a sidewall of which angle is unknown and plural reference microstructure patterns having sidewalls of which angles are known and are different to each other under plural SEM conditions having mutually different current values of electron beams or mutually different amplification values of photo-multiplier tubes;

a routine which measures a white band-width variation of each of the sample microstructure pattern and the plural reference microstructure patterns, the white band-width variation being an amount of change of a width of a white band at an edge portion of the microstructure pattern in the SEM image when the current value of the electron beam is changed or the amplification value of the photo-multiplier tube is changed;

a routine which obtains a correlation between an angle of a sidewall of a microstructure pattern and a white band-width variation, by using the measurement results of the white band-width variations of the plural reference microstructure patterns; and a routine which calculates the angle of the sidewall of the sample microstructure pattern, by using the correlation and the measurement result of the white band-width variation of the sample microstructure pattern.

10. The microstructure inspection method according to claim 1, wherein the correlation between the angle of the sidewall of the microstructure pattern and the white band-width variation is obtained by using simulation results of the white band-width variations calculated by a SEM simulator.

* * * * *